(12) United States Patent
Kulikovsky (10) Patent No.: US 9,739,725 B2
(45) Date of Patent: Aug. 22, 2017

(54) METHOD FOR CHARACTERIZING THE CATALYST STRUCTURE IN A FUEL CELL AND FUEL CELL DESIGN SUITABLE THEREFOR

(71) Applicant: FORSCHUNGSZENTRUM JÜLICH GMBH, Jülich (DE)

(72) Inventor: Andrei Kulikovsky, Nideggen-Abenden (DE)

( * ) Notice: Subject to any disclaimer, the term of this patent is extended or adjusted under 35 U.S.C. 154(b) by 139 days.

(21) Appl. No.: 14/763,062

(22) PCT Filed: Jan. 17, 2014

(86) PCT No.: PCT/DE2014/000021
§ 371 (c)(1),
(2) Date: Jul. 23, 2015

(87) PCT Pub. No.: WO2014/135135
PCT Pub. Date: Sep. 12, 2014

(65) Prior Publication Data
US 2015/0362441 A1    Dec. 17, 2015

(30) Foreign Application Priority Data

Mar. 2, 2013  (DE) .................. 10 2013 003 543

(51) Int. Cl.
*G01N 23/083*   (2006.01)
*H01M 8/04*     (2016.01)
*H01M 8/04298*  (2016.01)

(52) U.S. Cl.
CPC ...... *G01N 23/083* (2013.01); *H01M 8/04305* (2013.01); *G01N 2223/1003* (2013.01)

(58) Field of Classification Search
CPC .. H01M 8/141; H01M 8/1213; H01M 8/1004; H01M 8/02–8/0247; H01M 4/86
See application file for complete search history.

(56) References Cited

U.S. PATENT DOCUMENTS 7,400,705 B2 *  7/2008  Hoshino .......... G01N 23/201
                                                  378/80
2007/0238001 A1   10/2007  Koyama
2011/0008707 A1 *  1/2011  Muraoka ......... H01M 4/9016
                                                  429/483

OTHER PUBLICATIONS

Christina Roth et al: "In-situ XAFS fuel cell measurements of a carbon-supported Pt—Ru anode electocatalyst in hydrogen and direct methanol operation", Physical Chemistry Chemical Physics, vol. 4, No. 15, Jul. 3, 2002 (Jul. 3, 2002), pp. 3555-3557, XP055118054, ISSN: 1463-9076, DOI: 10.0039/b204293b, cited in the application—p. 3555; figure 1.

(Continued)

*Primary Examiner* — David J Makiya
*Assistant Examiner* — Soorena Kefayati
(74) *Attorney, Agent, or Firm* — Jordan and Koda, PLLC (57) ABSTRACT

A method for characterizing the catalyst structure in a fuel cell, and in particular the transmission X-ray absorption measurements (XAS), in which a novel fuel cell design is used. The fuel cell comprises a first (planar) electrode having a first catalyst, a second (planar) electrode having a second catalyst, and an electrolyte membrane disposed between the electrodes and having a layer thickness $l_m$, wherein the first electrode comprises at least one catalyst-free circular region having a radius $R1^{max}$. Contrary to what has been customary until now, the second electrode of the fuel cell according to the invention likewise comprises a catalyst-free circular region having a radius $R_2 < R_1^{max}$. Advantageously, $0.5\ l_m \leq [R_1^{max} - R_2] \leq 2\ l_m$ applies. Simulations prove that during these examinations, which capture only a narrow catalyst-containing sample ring, the local current density across the surface can be kept essentially constant, and therefore the captured catalyst particles are considerably more representative of the entire catalyst layer than in previously examinations using fuel cells in which the (Continued)

sample used has a completely circular measurement geometry.

17 Claims, 5 Drawing Sheets

(56) References Cited

OTHER PUBLICATIONS

Development of an In-Situ Cell for X-ray Absorption Measurements During Fuel Cell Operation C. Roth, N. Benker, M. Mazurek, F. Seheiba, H. Fuess; Advanced Engineering Materials (2005) vol. 7, No. 10, 952-956.
Dead Spot in the PEM Fuel Cell Anode A.A. Kulikovsky, Journal of the Electrochemical Society 160 (4), (2013), F 401-F 405.
Christina Roth et al: "In-situ XAFS fuel cell Measurements of a carbon-supported Pt—Ru anode electocatalyst in hydrogen and direct methanol operation", Physical Chemistry Chemical Physics, vol. 4, No. 15, Jul. 3, 2002 (Jul. 3, 2002), pp. 3555-3557, XP055118054, ISSN: 1463-9076, DOI: 10.1039/b204293b, cited in in the application—p. 3555; figure 1.
Ditty Dixon et al: "Space Resolved, in Operando X-ray Absorption Spectroscopy: Investigations on Both the Anode and Cathode in a Direct Methanol Fuel Cell", Journal of Physical Chemistry C, vol. 116, No. 13, Apr. 5, 2012 (Apr. 5, 2012), pp. 7587-7595, XP055115173, ISSN: 1932-7447, DOI: 10.1021/jp211321u Teil 2.2.
Wilson M S et al: "Thin-Film Catalyst Layers for Polymer Electrolyte Fuel Cell Electrodes" Journal of Applied Electrochemistry, Springer, Dordrecht, NL, vol. 22, No. 1, 1992, pp. 1-07, XP000461070, ISSN: 0021-891X, DOI: 10.10078/BF01093004, figure 4.

* cited by examiner

METHOD FOR CHARACTERIZING THE CATALYST STRUCTURE IN A FUEL CELL AND FUEL CELL DESIGN SUITABLE THEREFOR

The invention relates to a method for characterizing a fuel cell, in particular a membrane fuel cell, and in particular the catalyst structure of a cathode in such a fuel cell. The invention further relates to a special fuel cell design, which makes the above-mentioned characterization method possible in the first place.

BACKGROUND OF THE INVENTION

A large number of electrocatalytic reactions are considerably influenced by the structure and property of the catalyst. Efforts are therefore increasingly undertaken to examine the structural properties of fuel cells, and in particular of the catalytic layers of the particular electrodes.

While the identification and characterization of electrochemical reaction products take place exclusively during operation of the fuel cell, examinations regarding the characterization of the catalyst generally take place only prior to, and sometimes after, operation of the fuel cell.

Various examination methods are already known from the literature, which serve to arrive at a better understanding of the relationships between the catalyst structure and the resulting electrocatalytic activity of a membrane fuel cell (PEMFC). Methods used for structural characterization include microscopic, spectroscopic and diffraction methods, such as X-ray diffraction (XRD), transmission electron microscopy (TEM), and X-ray absorption spectroscopy (XAS). Methods may be classified as methods for bulk and/or surface characterization. Cyclic voltametry (CV) or electrochemical impedance spectroscopy are generally used for fuel cells, in order to determine the electrocatalytic properties of the examined materials.

Of the above-mentioned methods, transmission X-ray absorption spectroscopy (XAS) is one of the standard methods for determining the short-range order in molecules and solid bodies. It is therefore particularly suited to tracking changes in the catalyst structure or the catalyst oxidation state during operation, since it supplies detailed structural information about the immediate surroundings of the atom examined.

In transmission XAS, the ratio of X-ray intensity before and after passage through the sample is measured, and absorption is thus determined. From a physical perspective, the irradiation of a sample with X-rays results in an interaction, which is to say ionization of atoms or molecules due to absorption of the radiation results as a function of the energy content of the radiation. The neutral particles absorb one or more photons from a radiation field, which itself experiences weakening in the process, which is then detected.

During these measurements, the source used is advantageously X-ray radiation having variable energy. This allows for selection from the continuous spectrum, so that monochrome radiation having a defined energy content may be used, which is suitable for selectively ionizing certain atoms or molecules.

The ionization threshold specifically depends on the orbital from which the electron (photoelectron) is removed by the ionization, in addition, the interaction of the photoelectron with neighboring atoms changes the attenuation coefficient of the X-ray radiation in the vicinity of the ionization threshold, this change being directly dependent on the energy of the original ionized electron (photon), and is thus atom-specific.

Transmission XAS is a very simple method, however it requires the sample to be thin enough to allow at least a portion of the X-ray radiation to pass through. At a low X-ray radiation intensity, the samples would have to be extremely thin, for example in the range of one micrometer.

In the case of transmission XAS, both the interior of the sample and the surface thereof contribute to absorption. However, the contribution of the surface is generally much lower than that of the volume and can therefore generally not be separately determined. Ionization counters are used to determine X-ray intensity.

In fuel cell electrodes, the catalyst particles are generally the atoms that are of interest, and in particular the platinum particles. A transmission XAS measurement on a fuel cell in which the intensity of the radiation is measured after passing through a platinum-supported catalyst layer, for example, the energy dependence of the attenuation coefficient in the vicinity of the ionization threshold allows conclusions to be drawn about the surface adsorption compounds, the coordination numbers, and the neighbors of an adsorbed platinum atom.

The big advantage of the transmission XAS method is that these measurements can take place in situ, which is to say during operation of a fuel cell, so that the state of the catalyst in an operating fuel cell can be examined. A limiting factor that must be noted is that the transmission XAS method supplies information regarding a bulk property, while the catalytic material used, in particular, in a low-temperature fuel cell is, by nature, generally irregular, and is defined by way of particle size distribution and corresponding morphology.

In general, both an anodic catalyst and a cathodic catalyst are used in fuel cells. Without further modification, a direct transmission XAS measurement perpendicular to the cell plane of a fuel cell would thus include the superimposed signals of both electrodes. Thus, if the same catalyst, such as platinum, is used in the two electrodes, the measurement results would hardly be meaningful.

One deliberation is therefore based on the idea that a catalyst-free region should be created in one of the two catalyst layers of the electrodes, in the region of the X-ray, so that the measurement signal contains only the information for the catalyst on the other electrode.

In fuel cells, the cathode in particular is the object of many examinations, most potential losses are assumed to originate in the cathode, it is suspected that a better understanding of the states of the platinum atoms of the catalyst layer on the cathode side of a fuel cell will allow potential losses there to be minimized in the future.

In practice, in in situ transmission XAS examinations of a fuel cell that is in operation, a small circular region is removed from an electrode comprising the catalyst so as to produce information about the catalyst of the other electrode alone. It is known from [1] and [2], for example, to remove a region measuring approximately 0.2 cm$^2$ from the cathode in order to obtain better information on the anode catalyst. This catalyst is made of standard Pt—Ru (1:1) with 20 wt % on Vulcan XC-72, for example. At 1.2 mg/cm$^2$, the loading was selected considerably higher than is customary so as to generate a good signal-to-noise ratio.

Since the absorption edge of Ru has a different energy, transmission XAS examinations and evaluations are not impaired by the presence of Ru.

However, based on simulations, it was possible to show that removing the catalyst from the anode window on the anode side results in a considerable reduction of the membrane potential φ and in a considerable decrease in the local current on the cathode side in the direction of the center of the measurement window. Moreover, it was established that the characteristics of the local current on the surface of the cathode also exhibit a quite significantly irregular radial distribution. This would indicate that the catalyst particles appear to be in different states within the irradiated cathode window (measurement window), depending on whether they are located on the surface.

It may furthermore be concluded from this that the existing information, based on standard transmission XAS measurements for the characterization of the state and the structure of a catalyst, may potentially have to be called into question, since they, for the reasons mentioned above, cannot be representatively applied to the entire catalyst layer outside the spot, even though they provide overall information about the catalyst within the cathode window.

It is the object of the invention to provide a method for characterizing a catalyst in a membrane fuel cell in situ, which is to say during operation of a fuel cell, which allows more realistic information to be provided about the state and the structure of the catalyst of the entire catalyst layer of the fuel cell than has previously been possible according to the prior art.

It is a further object of the invention to make a fuel cell design available which is adapted to this method and at least partially optimized.

Transmission X-ray absorption spectroscopy (transmission XAS) is a particularly suitable method for allowing examination of the catalyst on a fuel cell to be carried out during operation. To this end, the standard XAS examination method for a cathode of a fuel cell provides for a portion of the anodic catalyst, generally platinum or a platinum/ruthenium mixture, to be removed in a small region, so as to create a transparent window for the X-rays impinging perpendicularly on the fuel cell and allow unimpaired access to the catalyst of the cathode, which is to say without further absorption by a catalyst on the anode. Optionally this means completely removing a corresponding portion of the anode, together with the catalyst. The generally circular catalyst-free window, hereafter referred to as the "anode window," has a radius, which is denoted by $R_a^{max}$. The subscript a indicates the anode. In terms of diameter, this anode window generally corresponds substantially precisely to that of the X-ray used in the XAS measurement.

In the standard measurement system, a monochrome X-ray is conducted almost perpendicularly onto the cell planes of the fuel cell, so that a region (measurement window) having an identical radius $R_K^{max}=R_a^{max}$ is irradiated on the cathode side (subscript K). Depending on the energy content of the X-ray radiation, the catalyst particles located in this region on the cathode side bring about absorption, and thus weakening of the X-ray, which is then detected. The detector is usually likewise limited to the region of the measurement window to ensure that only the X-rays weakened by the absorption within the measurement window are captured.

Within the scope of the invention, it was found based on simulations that, due to the removal of the catalyst on the anode side, this standard examination method disadvantageously results in the current distribution within the fuel cell being changed in the irradiated region on the opposing cathode side, in fact, it was possible to show that this results in an uneven distribution of the potential as a function of the radius of the measurement window. The local current on the cathode surface in the region of the irradiation (measurement window) exhibits a corresponding inhomogeneity since the removal of the catalyst from a portion of the anode surface severely interferes with the electrochemical processes that take place at the electrodes.

While the previously obtained measurement results in sum are characteristic of the catalyst in the irradiated region on the cathode side, they generally do not represent the current state of the catalyst particles on the entire cathode side. This, however, is the very information that was hoped to be obtained from this type of examination (XAS).

Based on simulation examinations, according to the invention, a novel design for a fuel cell comprising a first electrode and a second electrode is proposed, which can be used particularly well for in-situ XAS measurement and which advantageously has an essentially uniform distribution of the local current across the second electrode surface within the measurement region. In this way, it is possible to ensure that, by way of such a measurement, information about the catalyst of the second electrode is obtained, which corresponds to a characterization of all the catalyst particles on or in the second electrode that is considerably better than in the past, and which does not apply only to the measured region of the measurement window.

DESCRIPTION OF THE PREFERRED EMBODIMENTS

Figure 1:
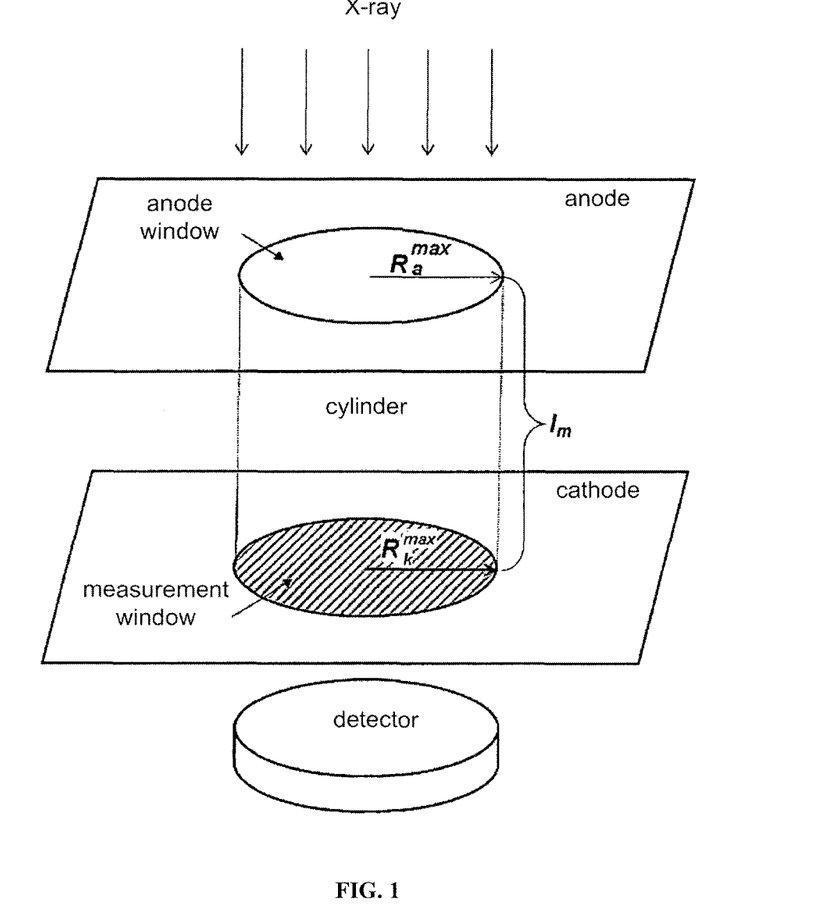
FIG. 1: shows a geometry of a planar fuel cell, as it is used according to the prior art for a transmission XAS measurement.
Figure 3:
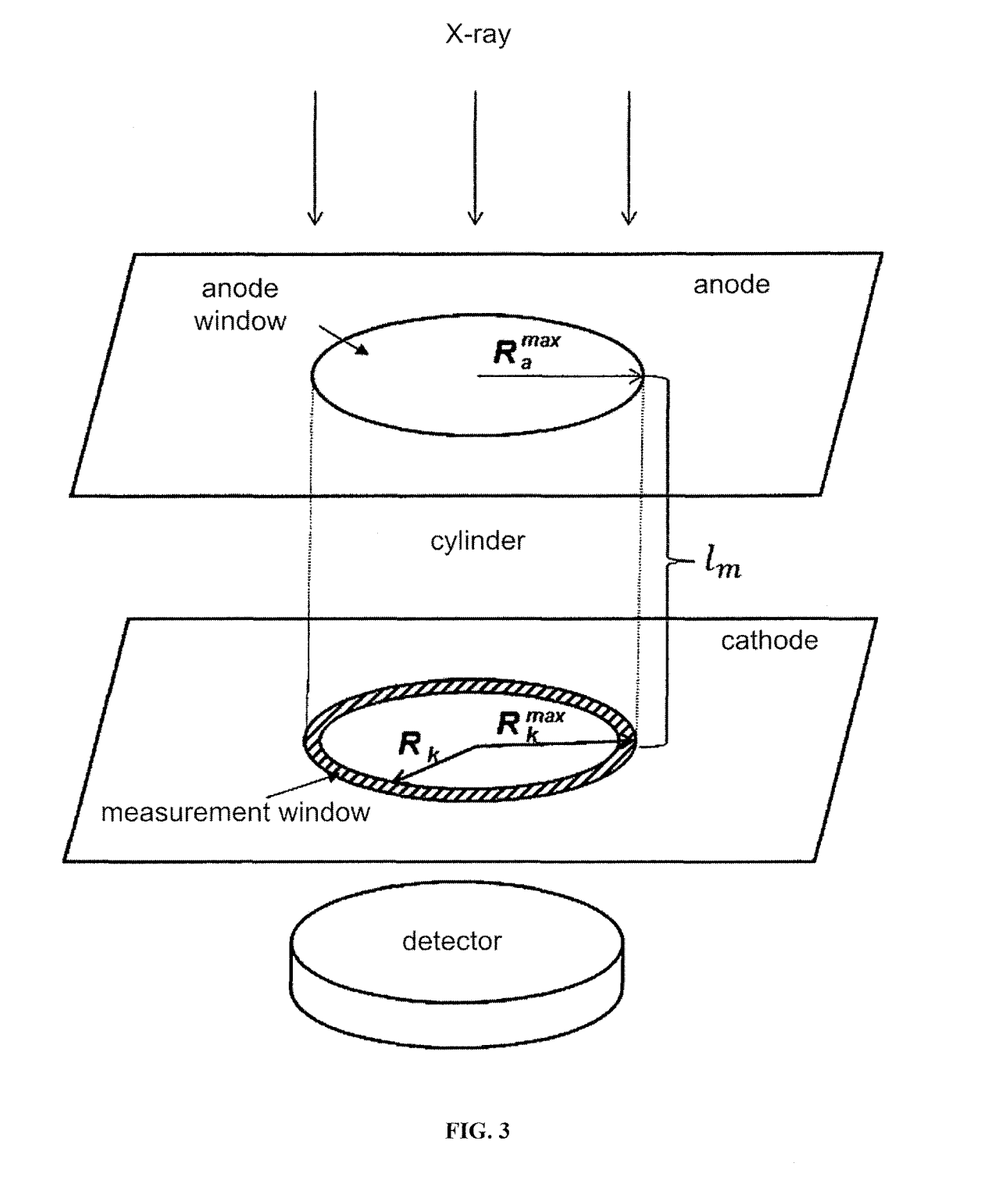
FIG. 3: shows a geometry of a planar fuel cell according to one exemplary embodiment of the invention, as it is used for a transmission XAS measurement according to the invention.

FIGS. 1 and 3 each show an variant embodiment of the examination system for a transmission X-ray absorption measurement, in which, in the viewing direction of the X-ray, the first electrode of the fuel cell represents an anode, and the second electrode of the fuel cell represents a cathode. As is indicated in the figures, the X-ray in this embodiment initially impinges perpendicularly on the anode and penetrates the electrolyte membrane and the cathode before it is then detected. The geometry of FIG. 1 corresponds to the Known prior art, white FIG. 3 shows an advantageous embodiment of the invention.

Even though the invention is described in more detail hereafter based on this variant embodiment, the invention is expressly not limited to this embodiment of a fuel cell, but explicitly also covers the reverse embodiment of a fuel cell comprising a cathode as the first electrode and an anode as the second electrode. The basic principle of the novel fuel cell design is not influenced by the specific design of the electrodes and functions in either case.

The model of a fuel cell underlying the simulation according to the prior art is shown in FIG. 1. So as to exclude the contribution of the catalyst located on the anode to the transmission X-ray absorption measurement, the anode catalyst is removed in a small circular region (anode window). A typical size for such a catalyst-free anode window is a circular region having a radius of approximately 0.2 to 0.4 cm, for example. The radius of the anode window is denoted by $R_a^{max}$ in the present example, the subscript a identifying the anode side. The surface area of the anode window is thus typically in the range of 10 to 50 mm².

According to the invention, the catalyst-free region on the anode is selected such that it is completely irradiated by the focused beam diameter of the X-ray. If the beam diameter of the X-ray is greater than that of the circular catalyst-free region on the anode, an appropriate diaphragm may optionally be provided between the X-ray source and the first electrode, wherein the opening of the diaphragm is identical to the catalyst-free region of the anode, which is to say likewise has a radius $R_a^{max}$.

For the sake of simplicity, an analogous circular region on the cathode side having an identical radius $r=R_a^{max}=R_k^{max}$ compared to the anode window is referred to as a "measurement window," the subscript $_k$ identifying the cathode side. This region is identical to the region on the cathode surface that is irradiated by the X-ray and is shown hatched in FIG. 1.

The cylindrical region of the electrolyte (polymer electrolyte membrane) disposed between the anode window on the anode side and the measurement window on the cathode side is referred to as "cylinder" in the present example. The cylinder height corresponds to the layer thickness $l_m$ of the electrolyte membrane, which is disposed between the anode and the cathode. For simplification, the anode and the cathode are each shown only as two-dimensional areas.

In this connection, the layer thicknesses of the individual catalyst layers are ignored in the evaluation since the proton conductivity of the catalyst layers is multiple times less than that of the membrane. In particular, the proton conductivity parallel to the cell plane is significantly lower for the catalyst layer than for the electrolyte membrane.

According to the invention, a fuel cell according to FIG. 3 is proposed as a novel design for carrying out transmission XAS measurements. The designations have been taken from and are identical to those of FIG. 1. The monochromatic X-ray is focused on the region $r=R_a^{max}$ and thus corresponds to the anode window.

In addition to removing catalyst from the circular region measuring $R_a^{max}$ (anode window) from the anode (first electrode), according to the invention a portion of the catalyst is now also removed from the measurement window on the opposing cathode (second electrode). Removing the catalyst advantageously takes place from inside likewise in a circular region, wherein the center of the measurement window is selected as the center of the catalyst-free region, and wherein a radius $R_k<R_k^{max}$ is selected.

Removing the cathode catalyst takes place in such a way that a narrow ring (sample ring) having the width $R_k^{max}-R_k$ comprising catalyst is preserved within the circular region (measurement window), the ring likewise being shown hatched in FIG. 3.

Based on the simulation, it was established that the selection of a ring geometry instead of a circular region on the cathode side causes the current resulting from the oxygen reduction reaction to flow in an essentially constant fashion within the sample ring, and independently of the radius, provided that the ring width is selected to be narrow and in particular corresponds to the membrane thickness $l_m$. According to the invention, the ring width $R_k^{max}-R_k$ is thus selected significantly smaller than $R_k^{max}$, and in the optimal case it is adapted to the layer thickness of the membrane $l_m$, which separates the anode and the cathode from each other.

In absolute values, the membrane should have a maximum layer thickness $l_m$ between 50 and 200 µm. As a result, values between 50 and 200 µm are likewise proposed as an advantageous ring width. For the existing radii for the anode window in the range of 0.2 to 0.4 cm, the assumption that $(R_k^{max}-R_k)<<R_k^{max}$ is thus met well.

During the XAS measurement, the X-ray penetrates the fuel cell in a region where $r=R_a^{max}=R_k^{max}$. The inner region of the measurement window where $r<R_k$ comprises no catalyst on either the anode side or the cathode side and thus does not contribute to the absorption of the X-ray. Only the catalyst within the sample ring where $R_k<r\le R_k^{max}$ on the cathode side, on which the X-ray radiation impinges, contributes to absorption, and thus to the weakening of the signal.

The outside diameter of the sample ring comprising the catalyst, on which the X-rays impinge, corresponds to that of the measurement window on the cathode side or that of the catalyst-free region (anode window) on the anode side. The ring width $R_k^{max}-R_k$ of the sample ring in the radial direction preferably corresponds to the layer thickness of the membrane $l_m$, or is selected to be less than the same.

This means that the ring width $R_k^{max}-R_k$ should ideally be less than approximately 100 µm for a membrane layer thickness of $l_m=100$ µm, for example. However, the scope of the invention also covers deviations in the sample ring width (membrane layer thickness ±50%). For the sake of clarity, the sizes of the sample ring width and of the membrane layer thickness are shown distorted in FIG. 3 and expressly do not correspond to real conditions.

The ring width $R_k^{max}-R_k$ should be established so as to satisfy two criteria. First, it must be ensured that the sample ring is narrow enough for the above-mentioned inhomogeneities, as they occur with the prior art, to be kept as low as possible. Secondly, however, the sample ring comprising the catalyst must also be wide enough for the weakened signal of the X-ray to still be qualitatively meaningful.

In the existing standard measurements, the complete region within the sample window where $r=R_k^{max}$ comprises catalyst and thus contributes to X-ray absorption. The surface area comprising catalyst corresponds to $F=\pi(R_k^{max})^2$.

In contrast, during the measurement according to the invention with an identical outside radius for the measurement window where $r=R_k^{max}$, considerably less catalyst would be available for absorbing the X-ray. The surface area of the sample ring comprising catalyst thus results as: $F=\pi[(R_k^{max})_2-R_k^2]$ and is therefore several times smaller than the surface area of the measurement window comprising catalyst, which according to the prior art contributes to the weakening of the X-ray.

It was found as a result of the simulation that the properties at the boundary $R=R_k$ are independent of the absolute value of the radius. So as to arrive at a meaningful measurement result, if is therefore proposed to appropriately increase the outside radius $R_k^{max}$ of the anode or measurement window compared to the radius that is customary from the prior art, so as to arrive at a larger ring surface area on the cathode side—despite the condition $R_k^{max}-R_k\sim l_m$. The maximum size to be set is limited by the X-ray.

Alternatively or cumulatively, however, excessive catalyst loading may also be considered. It is already known from the literature, for example, that catalyst loading with platinum was increased, for example, to at least 1.2 mg/cm² per electrode, for XAS examinations on fuel cells, which corresponds approximately to 6 times the customary loading. This should represent an acceptable compromise between a good signal-to-noise ratio for the detected X-ray and almost unchanged electrode properties, based on the current density distribution and the transport processes taking place there. The catalyst loading can thus also be appropriately increased in the present invention to arrive at an improved signal-to-noise ratio.

A simulation of this novel ring geometry according to the invention on the cathode side has confirmed that, under the described conditions of $R_k^{max} - R_k \ll R_k^{max}$, and at the same time $R_k^{max} - R_k \sim l_m$, the local current density distribution across the ring surface is essentially uniform and homogenous. This is an indication that the catalyst particles within the sample ring (which is to say the catalyst atoms captured by way of the measurement) as well as those outside the measurement region are now in essentially identical states.

The information that can be provided about the catalyst particles by way of such a transmission X-ray absorption measurement now advantageously represents the state of the entire catalyst layer on or in the second electrode, which is to say also for the region where $r > R_k^{max}$, which means the region of the catalyst layer located outside the actual measurement window.

The transmission XAS measurement itself is carried out analogously to the measurements known from the prior art. However, a variation according to the invention may be, for example, an adapted larger beam diameter for the X-ray used, or a larger diaphragm. In addition, a fuel cell comprising the novel inventive ring design is used.

Advantageously, the X-ray diameter is adapted to the anode window in such a way that the beam diameter corresponds exactly to that of the anode window. This ensures that the region of the anode window, and thus also of the measurement window or of the sample ring, is completely penetrated by the X-ray radiation, and thus corresponding qualitative information about the catalyst is possible Moreover, X-rays impinging outside the measurement window, and thus containing information about the catalyst of the first and second electrodes, can also be prevented from being included in the result and distorting the same.

As an alternative to adapting the geometry of the X-ray, or in combination therewith, the detector could also be appropriately adapted. For example, an additional diaphragm between the fuel cell and the detector could shield the region outside the measurement window.

In summary, it can be stated the present invention relates to a method for characterizing the catalyst structure in a fuel cell, and in particular to transmission X-ray absorption measurements (XAS), in which a novel fuel cell design is used. The fuel cell used comprises a first (planar) electrode having a first catalyst, a second (planar) electrode having a second catalyst, and an electrolyte membrane that is disposed between the electrodes and has a layer thickness $l_m$, wherein the first electrode comprises at least one catalyst-free circular region having a radius $R_1^{max}$. Contrary to what has previously been customary, the second electrode of the fuel cell according to the invention likewise comprises a catalyst-free circular region having a radius $R_2 > R_1^{max}$. Advantageously, $0.5\ l_m \leq [R_1^{max} - R_2] \leq 2\ l_m$ applies. The region located between $R_1^{max}$ and $R_2$ describes the so-called sample ring, which comprises the catalyst and is accordingly penetrated by the X-ray during the measurement.

Simulations prove that these examinations, which capture only a narrow catalyst-containing sample ring, allow the local current density across the surface to be kept essentially constant, and the captured catalyst particles are thus considerably more representative of the entire catalyst layer than in the examinations that were previously carried out with fuel cells in which the sample used is a completely circular measurement geometry.

At this point, the simulation underlying the invention and the model calculations, which resulted in the proposed novel fuel cell design, shall be addressed in greater detail.

The simulations conducted were based on a planar fuel cell model, which comprises two electrodes comprising catalyst and one interposed membrane having the layer thickness $l_m$ as the electrolyte, as is already described in [3]. The spatial conditions and assumptions disclosed there also formed the basis for the simulation presented herein. The fuel cells shown in highly schematic form in FIGS. 1 and 3 comprise an anode having a catalyst (top) and a cathode likewise having a catalyst (bottom). Both electrodes are shown in simplified form as surface areas. A cylindrical coordinate system is used, in which the z-axis is perpendicular to the fuel cell planes formed by the electrodes, and r=0 describes the center of the X-ray, which impinges perpendicularly on the fuel cell planes in the direction of the z-axis. r=0 is thus at the same time the center of the circular anode window, and consequently also establishes the center of the circular measurement window on the cathode side.

In each case, the membrane potential Φ, the excess potential of the oxygen reduction reaction $\eta_{ox}$, the current densities of the hydrogen oxidation reduction reaction $j_a$, and the current densities of the oxygen reduction reaction $j_c$ were calculated and entered.

The following Table 1 reflects the parameters on which the presented simulation was based, where ORR=oxygen reduction reaction. HOR=hydrogen oxidation reaction, ACL=anodic catalyst layer, and CCL=cathodic catalyst layer.

| | |
|---|---|
| ORR penetration factor, $\alpha_{ox}$ | 0.8 |
| ORR exchange current density $j_{ox}$ in [A cm$^{-2}$] | $10^{-6}$ |
| HOR penetration factor, $\alpha_{hy}$ | 1.0 |
| HOR exchange current density in the regular region $j_{hy}^y$ in [A cm$^{-3}$] | 1 |
| ORR equilibrium potential $E_{ox}^{eq}$ in [V] | 1.23 |
| HRR equilibrium potential $E_{hy}^{eq}$ in [V] | 0.0 |
| Proton conductivity of the membrane $\sigma_m$ in [Ω$^{-1}$ cm$^{-1}$] | 0.1 |
| Membrane layer thickness $l_m$ in [cm] | 0.0025 (25 μm) |
| Beam radius $R_a^{max}$ in $l_m$ [cm] | $10 * l_m = 0.025$ |
| Layer thickness of the exchange current transition region s in [cm] $10^{-3}$ | $R_a^{max} = 2.5 * 10^{-5}$ |
| HOR exchange current density (within the window)/ HOR exchange current density (outside the window) $k_s$ | $10^{-9}$ |
| Cell potential $j_c$ in [V] | 0.74513 |
| Cell current density in the regular region J, in [A cm$^{-2}$] | 0.5 |
| Cell temperature T in [K] | 273 + 65 |

Using the above-mentioned parameters, calculations were carried out on the potential and the current densities within the sample window on the cathode side and in the immediate surroundings thereof. The results are shown in FIGS. 2, 4, and 5.

For simplification and for abstraction, the radially dependent values were not assigned to an absolute radial position, but were related to normalized values, wherein these result as a ratio of the absolute radial position r to $R_a^{max}$. With r=0, and thus $r/R_a^{max} = 0$, the center of the sample window is provided. The region within the sample window is represented by $0 \leq r/R_a^{max} \leq 1$, wherein $r/R_a^{max} = 1$ represents the outer ring on which, on the anode side, the catalyst-free region and the catalyst-containing region abut each other. Values with $r/R_a^{max}>1$ identify positions outside the sample window.

The figures show the calculations for a region from the center to twice the radius of the sample window/measurement, in each case.

A sample calculation can be found in Table 1 below, in which the membrane layer thickness was established at 25 μm, for example. The first line indicates the reference value according to the prior art for a circular measurement window.

| $R_a^{max} = R_k^{max}$ [mm] | Anode window surface area [mm²] | $R_k^{max}$-Rk [mm] | Measurement window surface area [mm²] | Measurement window/anode window |
|---|---|---|---|---|
| 0.25 | 0.20 | 0 | 0.20 | 100% |

| $R_a^{max} = R_k^{max}$ [mm] | | $R_k^{max}$-Rk [mm] | Sample ring surface area [mm²] | Sample ring/standard sample window |
|---|---|---|---|---|
| 0.25 | 0.20 | 0.025 | 0.04 | 20% |
| 1.26 | | 0.025 | 0.2 | 100% |
| 0.65 | | 0.050 | 0.2 | 100% |

In FIGS. 2, 4 and 5, these simulated values are plotted against the radial distance $r/R_a^{max}$ that has been normalized to the maximum radius of the anode window, in each case. The center of the measurement window r=0 corresponds to x=0. The radii of the anode window $R_a^{max}$ and of the measurement window $R_k^{max}$ thus correspond to x=1. The x-values >1 accordingly denote the region outside the measurement window.

FIG. 2 shows the simulated results for the standard case, as they result from the geometry illustrated in FIG. 1, while FIGS. 4 and 5 show the results for an advantageous embodiment of the fuel cell according to the invention, as they result from the geometry of the sample ring proposed in FIG. 3.

Figure 2A:
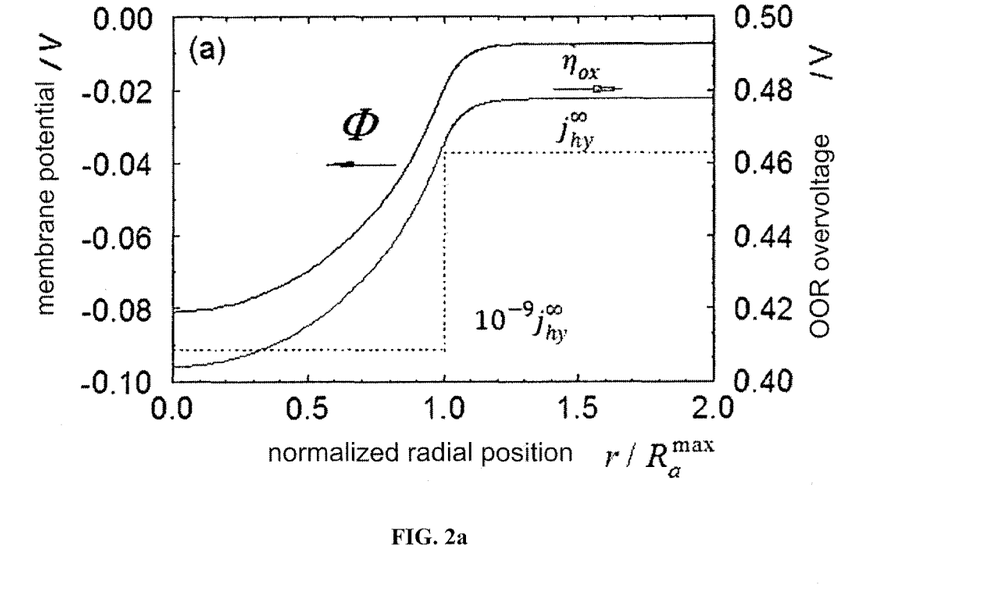
FIG. 2: shows model calculations for a fuel cell having a geometry according to FIG. 1.

The absence of the catalyst in the anode window is reflected by the drastic decrease in current exchange density for the hydrogen oxidation reaction, as shown in FIG. 2a. The potential outside the measurement window is just under 0.5 V (0.493 V). Toward the edge of the measurement window, a continuous decrease of the potential is apparent, which then drops to approximately 0.42 V in the interior of the measurement window. This corresponds to a decrease from outside the measurement window to the center of the measurement window of approximately 0.08 V.

Figure 2B:
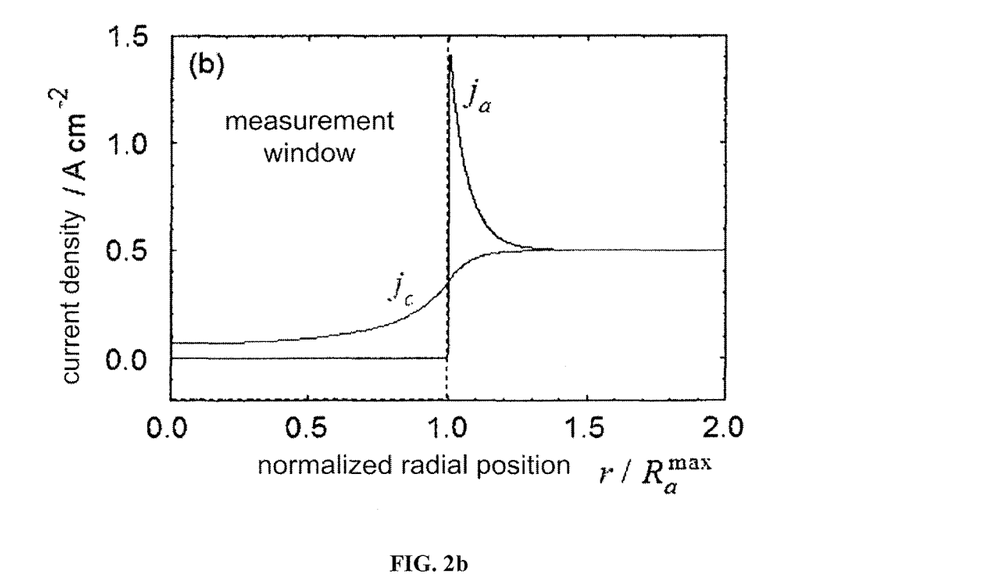

The corresponding current densities are reflected in FIG. 2b. The two exchange current densities (current density of the hydrogen oxidation reduction reaction $j_a$, current density of the oxygen reduction reaction $j_c$) outside the measurement window are approximately 0.5 A/cm². Toward the edge of the measurement window, the current density of the hydrogen oxidation reduction reaction $j_a$ steeply increases to approximately 1.4 A/cm², only to then remain constant within the measurement window at 0 A/cm². The current density of the oxygen reduction reaction $j_c$, in contrast, continuously decreases toward the edge of the measurement window, only to then be approximately 0.1 A/cm² at the center.

Figure 4A:
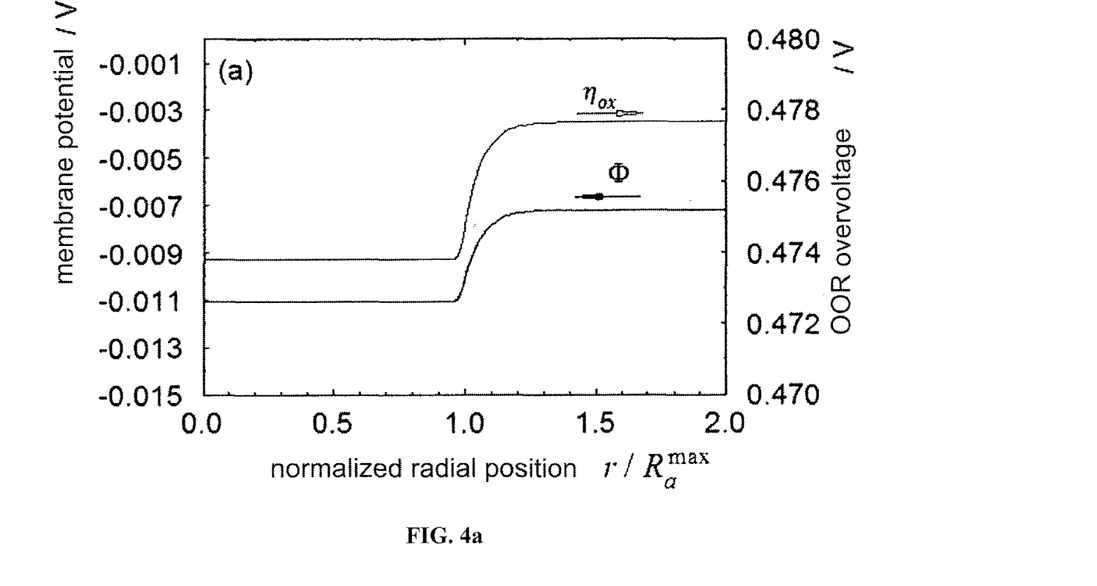
FIG. 4: shows a model calculations for a fuel cell having a geometry according to FIG. 3.
Figure 4B:
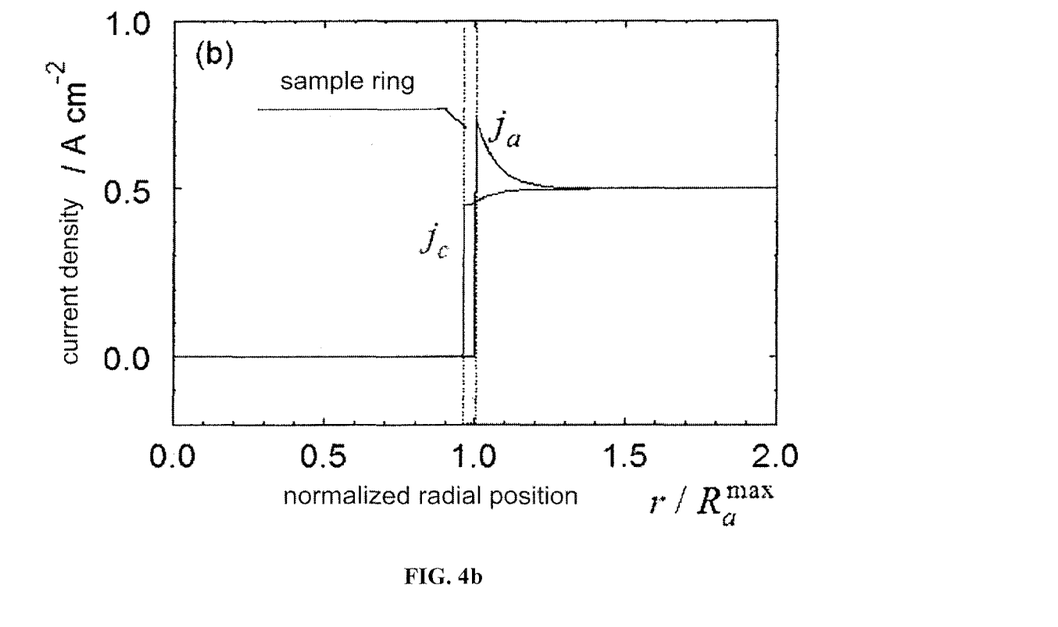
Figure 5:
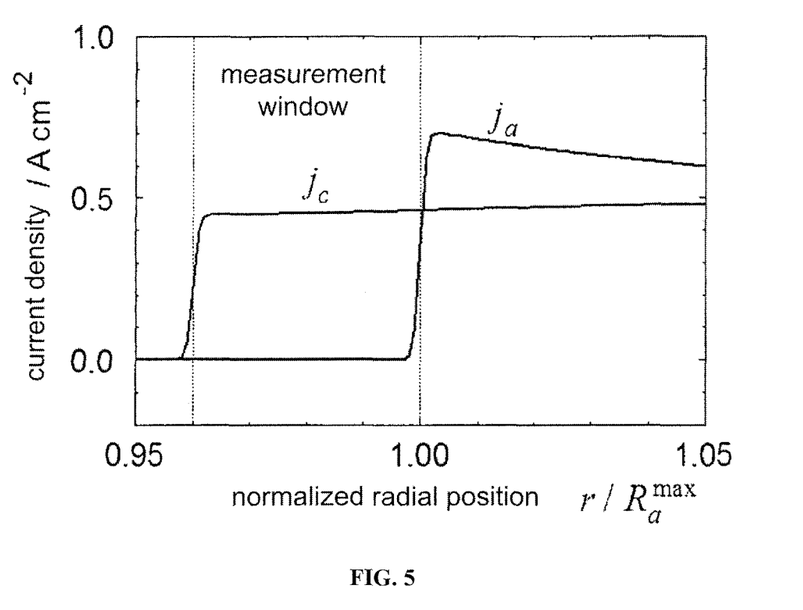
FIG. 5: shows an enlarged detail from FIG. 4b.

The use of a fuel cell according to the invention having a ring-shaped measurement region, in contrast, results in the values shown in FIGS. 4a, 4b and 5.

Here as well the absence of the catalyst in the anode window results in a decrease in current exchange density for the hydrogen oxidation reaction, as shown in FIG. 4a. However, the drop of the potential is considerably less here. At approximately 0.475 V, the potential outside the measurement window is slightly lower than usual here. Toward the edge of the measurement window, a slight continuous decrease of the potential to approximately 0.474 V is again apparent. However, contrary to the standard geometry, this value remains essentially constant across the entire measurement surface area. This corresponds to a decrease from outside the measurement window to the center of the measurement window of only approximately 0.01 V.

The corresponding current densities for the fuel cell according to the invention are reflected in FIG. 4b. The two exchange current densities (current density of the hydrogen oxidation reduction reaction $j_a$, current density of the oxygen reduction reaction $j_c$) outside the measurement window are approximately 0.5 A/cm². Toward the edge of the measurement window, the current density of the hydrogen oxidation reduction reaction $j_a$ increases to only approximately 0.7 A/cm², only to then remain constant within the measurement window at 0 A/cm². The current density of the oxygen reduction reaction $j_c$, in contrast, continuously decreases toward the edge of the measurement window. An essentially constant value of approximately 0.45 A/cm² develops in the region of the ring surface, which drops steeply to 0 A/cm² only in the region of $r=R_k$ in the direction of the center.

LITERATURE CITED IN THE APPLICATION

[1] Christina Roth, Nathalie Martz, Thorsten Buhrmester, Joachim Scherer and Hartmut Fuess; Phys. Chem. Chem. Phys., 2002, 4, 3555-3557.
[2] C. Roth, N. Benker, M. Mazurek, F. Scheiba, H. Fuess; Advanced Engineering Materials (2005) Vol. 7, No. 10, 952-956.
[3] A. A. Kulikovsky. J. Electrochem. Soc, 180 (4), (2013), F 401-F 405.

The invention claimed is:

1. A fuel cell for carrying out a transmission X-ray absorption measurement (XAS), comprising:
    a first electrode having a first catalyst;
    a second (planar) electrode having a second catalyst; and
    an electrolyte membrane that is disposed between the electrodes and has a layer thickness $l_m$, wherein the first electrode comprises at least one catalyst-free circular region having a first radius, and the second electrode comprises at least one catalyst-free circular region having a second radius less than the first radius.

2. The fuel cell according to claim 1, wherein the center of the catalyst-free region of the first electrode and the center of the catalyst-free region of the second electrode are located on an axis which, during the X-ray absorption measurement, is identical to a beam axis of the X-ray.

3. The fuel cell according to claim 1, wherein said first radius of the catalyst-free region of the first electrode is between 0.1 and 10.0 mm.

4. A fuel cell according to claim 1, wherein the layer thickness $l_m$ of the membrane is no more than 200 μm.

5. A fuel cell according to claim 1, wherein said second radius of the catalyst-free region of the second electrode is within a range between a first value, which equals the first radius minus twice said thickness $l_m$, and a second value, which equals the first radius minus one-half said thickness $l_m$.

6. A fuel cell according to claim 1, comprising a polymer electrolyte membrane.

7. A fuel cell according to claim 1, having a catalyst loading on the second electrode of more than 0.5 mg/cm$^2$.

8. A fuel cell according to claim 1, wherein the second electrode is a cathode.

9. A fuel cell according to claim 1, wherein the catalyst of the second electrode comprises platinum.

10. The fuel cell according to claim 1, wherein said first radius of the catalyst-free region of the first electrode is between 0.5 and 2.0 mm.

11. A fuel cell according to claim 1, wherein the layer thickness $l_m$ of the membrane is no more than 100 μm.

12. A fuel cell according to claim 1, wherein the layer thickness $l_m$ of the membrane is between 1 and 50 μm.

13. A fuel cell according to claim 1, having a catalyst loading on the second electrode of more than 1.0 mg/cm$^2$.

14. A fuel cell according to claim 1, having a catalyst loading on the second electrode between 1.5 and 2.5 mg/cm$^2$.

15. A method for carrying out transmission X-ray absorption measurements (XAS) using a fuel cell according to claim 1, the method comprising:

irradiating said fuel cell, during operation of the fuel cell, with X-ray radiation having a beam radius that is identical to the said first radius of the catalyst-free circular region of the first electrode, wherein at least a portion of the X-ray radiation passes through the fuel cell; and detecting said portion of the X-ray radiation with a detector.

16. The method according to claim 15, wherein said detecting comprises:

exclusively detecting a circular region having a radius that is identical to the first radius of the catalyst-free circular region of the first electrode.

17. The method according to claim 15, wherein said irradiating comprises:

irradiating said fuel cell with X-ray radiation that shines through the catalyst-free region of the first electrode onto a partially catalyst-free region of the second electrode, and thereafter a weakened signal, as said portion of the X-ray radiation that passes through the fuel cell, is detected by said detector.

* * * * *